United States Patent

Floyd et al.

[11] Patent Number: 4,694,002
[45] Date of Patent: Sep. 15, 1987

[54] BENZOTHIAZEPINE DERIVATIVES

[75] Inventors: David Floyd, Pennington; Karnail Atwal, Cranbury, both of N.J.

[73] Assignee: E. R. Squibb & Sons, Inc., Princeton, N.J.

[21] Appl. No.: 898,570

[22] Filed: Aug. 21, 1986

[51] Int. Cl.⁴ .................. A61K 31/55; C07D 281/10
[52] U.S. Cl. ................................ 514/211; 540/491
[58] Field of Search ....................... 540/491; 514/211

[56] References Cited

U.S. PATENT DOCUMENTS 3,075,967 1/1963 Krapcho ............................. 540/491
4,590,188 5/1986 Takeda et al. ..................... 540/491

OTHER PUBLICATIONS

Pharmazie, vol. 35, pp. 680–681.
Pharmazie, vol. 38, pp. 827–828.
J. Med. Chem., vol. 9, p. 191, (1966).
J. Med. Chem., vol. 6, p. 544, (1963).
Chem. Pharm. Bull., vol. 31, p. 1780, (1963).

Primary Examiner—Robert T. Bond
Attorney, Agent, or Firm—Lawrence S. Levinson; Donald J. Barrack

[57] ABSTRACT

Calcium channel blocking activity is exhibited by compounds having the formula

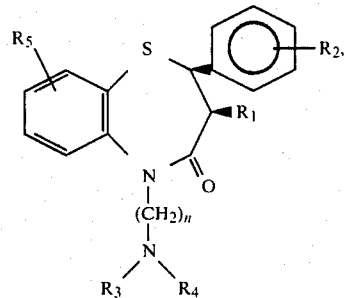

or a pharmaceutically acceptable salt thereof, wherein the stereochemistry at the chiral centers in the 3 and 4-positions of the benzothiazepine nucleus is cis, and wherein
$R_1$ is alkyl, aryl, arylalkyl, alkenyl or alkynyl;
$R_2$ and $R_5$ are each independently hydrogen, alkyl of 1 to 4 carbon atoms, alkoxy of 1 to 4 carbon atoms, halogen or trifluoromethyl; and
$R_3$ and $R_4$ are each independently alkyl or cycloalkyl or $R_3$ and $R_4$ together with the nitrogen atom to which they are attached are pyrrolidinyl, piperidinyl or morpholinyl.

15 Claims, No Drawings

BENZOTHIAZEPINE DERIVATIVES

BACKGROUND OF THE INVENTION

U.S. Pat. No. 3,075,967, issued Jan. 29, 1963 to John Krapcho describes benzothiazepine derivatives having the formula

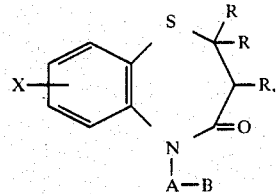

and salts thereof, wherein X is hydrogen, lower alkyl, lower alkoxy, nitro, halo or trifluoromethyl; each R is hydrogen, lower alkyl, an X-substituted phenyl lower alkyl, an X-substituted phenyl, furyl, thienyl, pyridyl or piperonyl; A is lower alkylene (preferably ethylene and propylene); and B is a basic nitrogen-containing radical of less than twelve carbon atoms. Among the suitable radicals represented by the symbol B are: amino; (lower alkyl)amino; di(lower alkyl)amino; (hydroxylower alkyl)amino; di(hydroxy-lower alkyl)amino; phenyl(-lower alkyl)amino; N-(lower alkyl)phenyl (lower alkyl)amino; and saturated 5 to 6 membered monocyclic heterocyclic radicals of less than twelve carbon atoms. The compounds are described as useful for the treatment of Parkinsonism and as tranquilizers.

In *J. Med. Chem.*, 6:544 (1963) and *J. Med. Chem.*, 9:191 (1966), Krapcho et al. discuss compounds falling within the scope of the above patent.

In *Chem. Pharm. Bull.*, 31(5):1780 (1963), Ohno et al. describe cis benzothiazepine derivatives having the formula

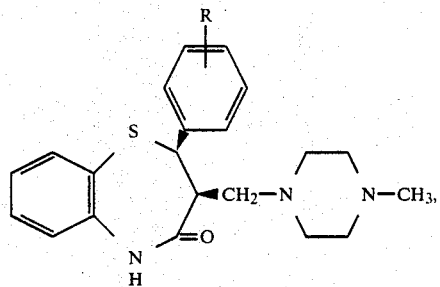

wherein R is hydrogen, 4-methyl, 4-chloro, 4-methoxy, 3-methyl and 3-chloro, as having anti-ulcer and gastric secretory inhibiting activities.

In *Pharmazie*, 35:680 (1980) and *Pharmazie*, 827 (1983), Levai et al. describe benzothiazepines having the formula

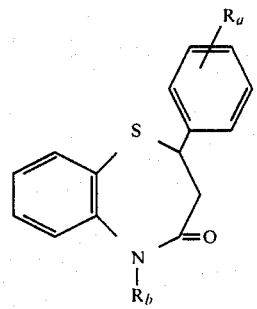

wherein $R_a$ is hydrogen, 2- or 4-methoxy, 4-isopropyl, 2- or 3-nitro, 2- or 4-chloro, 2,4-, 3,4-or 2,6-dichloro, 2,5-dimethoxy, or 3-hydroxy-4-methoxy, and $R_b$ is hydrogen, carboxymethyl, 2-carboxyethyl, 1-carboxyethyl, or 2-(ethoxycarbonyl)ethyl, and trans benzothiazpines having the formula

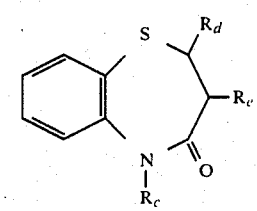

wherein $R_c$ is hydrogen or $-(CH_2)_n-COOH$ and n is 0, 1 or 2, $R_d$ is phenyl, specified substituted phenyl groups, 1- or 2-naphthyl, 3-chromonyl, 2-furyl, or 2-thienyl, and $R_e$ is hydrogen, methyl, acetylamino, or phenyl.

Diltiazem, a commercial calcium channel blocking agent, is a cis benzothiazepine having in the 3-position an acetyloxy group. The structural formula of diltiazem is

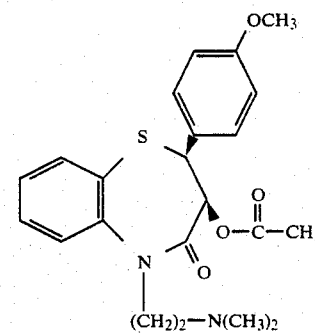

Diltiazem is representative of a large group of cis benzothiazepines having in the 3-position a substituent linked to the benzothiazepine nucleus via an oxygen atom.

BRIEF DESCRIPTION OF THE INVENTION

It has now been found that cis isomers having the formula

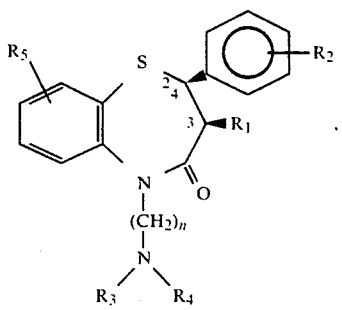

and the pharmaceutically acceptable salts thereof, have calcium channel blocking activity. These compounds are cis benzothiazepines having in the 3-position of the benzothiazepine nucleus a substituent linked to the nucleus via a carbon atom. In formula I, and throughout the specification, the symbols are as defined below.

$R_1$ is alkyl, aryl, arylalkyl, alkenyl or alkynyl;

$R_2$ and $R_5$ are each independently hydrogen, alkyl (of 1 to 4 carbon atoms), alkoxy (of 1 to 4 carbon atoms), halogen or trifluoromethyl; and $R_3$ and $R_4$ are each independently alkyl or cycloalkyl or $R_3$ and $R_4$ together with the nitrogen atom to which they are attached are pyrrolidinyl, piperidinyl or morpholinyl.

Listed below are definitions of various terms used to describe the benzothiazepines of this invention. These definitions apply to the terms as they are used throughout the specification (unless they are otherwise limited in specific instances) either individually or as part of a larger group.

The terms "alkenyl" and "alkynyl" refer to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (—NH$_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl or carboxyl groups.

The terms "alkyl" and "alkoxy" refer to both straight and branched chain groups. Those groups having 1 to 10 carbon atoms are preferred.

The term "cycloalkyl" refers to groups having 3, 4, 5, 6 or 7 carbon atoms.

The term "alkanoyl" refers to groups having the formula

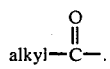

Those alkanoyl groups having 2 to 11 carbon atoms are preferred.

The term "halogen" refers to fluorine, chlorine, bromine and iodine.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, fumarate, citrate, succinate, benzoate, ascorbate, salicylate, methanesulfonate, benzenesulfonate, toluenesulfonate, lactate and the like.

The carbon atoms in the 2 and 3-positions of the benzothiazepine nucleus of the compounds of formula I are asymmetric carbons. The compounds of formula I, therefore, exist as enantiomeric mixtures. This invention is directed to those compounds of formula I wherein the relative stereochemistry at the chiral centers in the 2 and 3-positions of the benzothiazepine nucleus is cis.

DETAILED DESCRIPTION OF THE INVENTION

The compounds of formula I, and the pharmaceutically acceptable salts thereof, are useful as cardiovascular agents. These compounds act as vasodilators and are useful as anti-hypertensive agents. By the administration of a composition containing one (or a combination) of the compounds of this invention, the blood pressure of a hypertensive mammalian (e.g., human) host is reduced. Daily doses of about 0.1 to 100 mg per kilogram of body weight per day, preferably about 1 to about 50 mg per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensive may also be useful as antiarrhythmic agents, as anti-anginal agents, as antifibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The cis benzothiazepines of formula I can be prepared by epimerization of the corresponding trans benzothiazepine. This can be accomplished by treating the appropriate trans benzothiazepine with a strong base, such as lithium diisopropylamide, at a reduced temperature (less than about −20° C., preferably about −78° C. or less). The reaction can be quenched with an organic acid, e.g., acetic acid.

The starting trans benzothiazepines are known, and can be prepared using the methodology described in U.S. Pat. No. 3,075,967 issued Jan. 29, 1963. This comprises reacting a 2-aminothiophenol having the formula

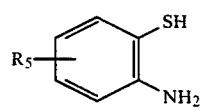

with a cinnamic acid derivative having the formula

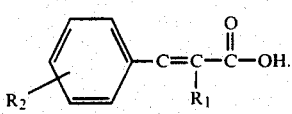

The following examples are specific embodiments of this invention.

EXAMPLE 1

(cis)-5-[2-(Dimethylamino)ethyl]-2,3-dihydro-3-methyl-2-phenyl-1,5-benzothiazepin-4(5H)-one, monohydrochloride A solution of diisopropylamine (1.2 g; 12 mmole) in 12 ml of dry tetrahydrofuran was cooled in an ice bath and treated with a 1.6M solution of n-butyl lithium in hexane (7.35 ml; 11.8 mmole) under argon. The reaction mixture was allowed to stir for ~30 minutes and was cooled to −78° C. A solution of (trans)-5-[2-(dimethylamino)ethyl]-2,3-dihydro-3-methyl-2-phenyl-1,5-benzothiazepin-4(5H)-one (1.8 g; 6 mmole) in 2 ml of tetrahydrofuran was added slowly to a solution of lithium diisopropylamide in tetrahydrofuran at −78° C. under argon and allowed to stir at −78° C. for 5 hours. An aliquot (~100 mg) was syringed out after 4 hours of reaction time and quenched with acetic acid/tetrahydrofuran (0.5/0.5 ml), diluted with ether, washed with saturated potassium bicarbonate, dried over anhydrous magnesium sulfate, and concentrated in vacuo. The NMR of the product indicated a 16/4 cis/trans ratio.

When the whole reaction mixture was quenched with acetic acid/tetrahydrofuran (2/2 ml) and worked up as above, NMR showed a 33/67 cis/trans ratio. 1.3 g of the product mixture was purified by flash chromatography eluting with 5% methanol in acetone to yield 0.3 g of pure cis compound
0.46 g of mixture of cis and trans (more cis)
0.54 g of pure trans compound.

To a solution of the cis amine (0.3 g; 1 mmole) in 1 ml of dichloromethane was added 10 ml of etheral hydrochloric acid. The reaction mixture was stirred at room temperature for ~30 minutes, then concentrated in vacuo and diluted with ether, stirred overnight, filtered and dried to yield 0.25 g of the title compound, melting point 203°–204° C.

Analysis Calc'd for $C_{20}H_{24}N_2OS.HCl.0.95H_2O$: C, 60.94; H, 6.53; N, 7.10; Cl, 8.99; S, 8.13 Found: C, 60.94; H, 6.52; N, 6.91; Cl, 9.09; S, 7.83

EXAMPLE 2

(cis)-5-[2-(Dimethylamino)ethyl]-2,3-dihydro-2-(4-methoxyphenyl)-3-methyl-1,5-benzothiazepin-4(5H)-one, monohydrochloride A solution of freshly distilled diisopropylamine (0.66 g; 0.0066 mole) in 10 ml of dry tetrahydrofuran was cooled in an ice bath and treated with a 1.0 M solution of n-butyl lithium in hexane (6.3 ml; .0063 mole) under argon. The reaction mixture was allowed to stir for ~30 minutes at 0° C. and then cooled to −78° C. A solution of (trans)-5-[2-(dimethylamino)ethyl]-2,3-dihydro-2-(4-methoxyphenyl)-3-methyl-1,5-benzothiazepin-4(5H)-one (1.06 g; 0.0029 mole) in 2 ml of tetrahydrofuran was then added to this mixture and allowed to stir at −78° C. for 4 hours. The reaction mixture was then cooled to −100° C. with methanol and liquid nitrogen and quenched slowly with a cold solution of acetic acid/tetrahydrofuran (0.5/0.5 ml). It was then stirred for ~10 minutes and allowed to warm to room temperature, diluted with water and extracted with dichloromethane, dried over anhydrous magnesium sulfate and concentrated in vacuo to yield 0.6 g of crude product, which was purified by flash chromatography, eluting with 9/1 (dichloromethane/methanol). The purified product was dissolved in dichloromethane (1 ml) and treated with ether/hydrochloric acid (30 ml), stirred for ~15 minutes, concentrated in vacuo and purified on a preparative plate (7/3 ethyl acetate/methanol). The resulting solid was crystallized from acetonitrile to give 0.087 g of the title product, melting point 167°–168° C.

Analysis Calc'd for $C_{21}H_{26}N_2O_2S.HCl.0.16H_2O$: C, 61.55; H, 6.71; N, 6.85; Cl, 8.66; S, 7.80 Found: C, 61.55; H, 6.65; N, 7.11; Cl, 8.66; S, 7.75

What is claimed is:

1. A compound having the formula

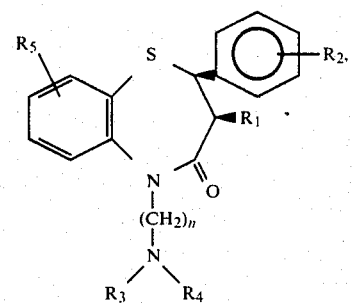

or a pharmaceutically acceptable salt thereof, wherein the stereochemistry at the chiral centers in the 2 and 3-positions of the benzothiazepine nucleus is cis, and wherein $R_1$ is alkyl, aryl, arylalkyl, alkenyl or alkynyl;

$R_2$ and $R_5$ are each independently hydrogen, alkyl of 1 to 4 carbon atoms, alkoxy of 1 to 4 carbon atoms, halogen or trifluoromethyl; and $R_3$ and $R_4$ are each independently alkyl or cycloalkyl or $R_3$ and $R_4$ together with the nitrogen atom to which they are attached are pyrrolidinyl, piperidinyl or morpholinyl.

2. A compound in accordance with claim 1 wherein $R_1$ is alkyl.

3. A compound in accordance with claim 1 wherein $R_1$ is aryl.

4. A compound in accordance with claim 1 wherein $R_1$ is arylalkyl.

5. A compound in accordance with claim 1 wherein $R_1$ is alkenyl.

6. A compound in accordance with claim 1 wherein $R_1$ is alkynyl.

7. A compound in accordance with claim 1 wherein $R_1$ is methyl.

8. A compound in accordance with claim 1 wherein $R_2$ is hydrogen.

9. A compound in accordance with claim 1 wherein $R_5$ is hydrogen.

10. A compound in accordance with claim 1 wherein $R_2$ and $R_5$ are hydrogen.

11. A compound in accordance with claim 1 wherein $R_3$ and $R_4$ are each alkyl.

12. A compound in accordance with claim 1 wherein $R_3$ and $R_4$ are each methyl.

13. The compound in accordance with claim 1, (cis)-5-[2-(dimethylamino)ethyl]-2,3-dihydro-3-methyl-2- phenyl-1,5-benzothiazepin-4(5H)-one, or a pharmaceutically acceptable salt thereof.

14. The compound in accordance with claim 1, (cis)-5-[2-(dimethylamino)ethyl]-2,3-dihydro-2-(4-methoxyphenyl)-3-methyl-1,5-benzothiazepin-4(5H)-one, or a pharmaceutically acceptable salt thereof.

15. A method of controlling blood pressure in a mammalian host in need thereof, which comprises administering to said host an effective amount of a compound having the formula

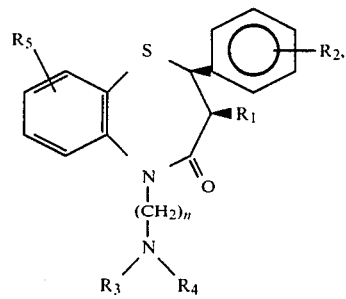

or a pharmaceutically accpetable salt thereof, wherein the stereochemistry at the chiral centers in the 2 and 3-position of the benzothiazepine nucleus is cis, and wherein $R_1$ is alkyl, aryl, arylalkyl, alkenyl or alkynyl;

$R_2$ and $R_5$ are each independently hydrogen, alkyl of 1 to 4 carbon atoms, alkoxy of 1 to 4 carbon atoms, halogen or trifluoromethyl; and $R_3$ and $R_4$ are each independently alkyl or cycloalkyl or $R_3$ and $R_4$ together with the nitrogen atom to which they are attached are pyrrolidinyl, piperidinyl or morpholinyl.

* * * * *

UNITED STATES PATENT AND TRADEMARK OFFICE
CERTIFICATE OF CORRECTION

PATENT NO. : 4,694,002

DATED : September 15, 1987

INVENTOR(S) : David Floyd and Karnail Atwal

It is certified that error appears in the above-identified patent and that said Letters Patent is hereby corrected as shown below:

In column 8, line 15 "accpetable" should be --acceptable--.

Signed and Sealed this

Twenty-seventh Day of September, 1988

Attest:

DONALD J. QUIGG

Attesting Officer    Commissioner of Patents and Trademarks